United States Patent [19]
Harada et al.

[11] Patent Number: 5,759,157
[45] Date of Patent: Jun. 2, 1998

[54] BLOOD PRESSURE MEASURING APPARATUS

[75] Inventors: Chikao Harada; Yoshihisa Miwa, both of Komaki, Japan

[73] Assignee: Colin Corporation, Komaki, Japan

[21] Appl. No.: 750,820

[22] PCT Filed: May 23, 1996

[86] PCT No.: PCT/JP96/01412

§ 371 Date: Dec. 10, 1996

§ 102(e) Date: Dec. 10, 1996

[87] PCT Pub. No.: WO96/38081

PCT Pub. Date: Dec. 5, 1996

[30] Foreign Application Priority Data

May 30, 1995 [JP] Japan .................. 7-132163

[51] Int. Cl.$^6$ .................................................. A61B 5/00
[52] U.S. Cl. .............. 600/494; 600/493; 600/495
[58] Field of Search ..................... 600/485, 490, 600/493–7, 561

[56] References Cited

U.S. PATENT DOCUMENTS

| | | | |
|---|---|---|---|
| 4,850,368 | 7/1989 | Miyawaki . | |
| 5,014,714 | 5/1991 | Millay et al. | 600/493 |
| 5,054,495 | 10/1991 | Uemura et al. | 600/493 |
| 5,099,853 | 3/1992 | Uemura et al. | 600/494 |
| 5,103,830 | 4/1992 | Shinomiya | 600/493 |
| 5,135,003 | 8/1992 | Souma | 400/493 |

FOREIGN PATENT DOCUMENTS

| | | |
|---|---|---|
| A-61-79442 | 4/1986 | Japan . |
| U-2-45706 | 3/1990 | Japan . |
| A-5-200005 | 8/1993 | Japan . |
| A-6-154174 | 6/1994 | Japan . |

*Primary Examiner*—Robert L. Nasser
*Attorney, Agent, or Firm*—Oliff & Berridge, PLC

[57] ABSTRACT

When it is judged by a blood-pressure-abnormality judging means that a first blood pressure value determined by a first blood pressure determining means, based on a pulse-synchronous signal produced while a pressure of a cuff is slowly increased, is abnormal, a second blood pressure value is determined by a second blood pressure determining means without needing another first blood pressure value determination. Thus, it is possible to eliminate the time necessary for decreasing and re-increasing the pressure of the cuff, thereby reducing the discomfort of the patient. Additionally, since the present blood pressure measuring apparatus can measure a second blood pressure value relatively speedily, it does not need a device for removing noise from the signal.

9 Claims, 6 Drawing Sheets

BLOOD PRESSURE MEASURING APPARATUS

FIELD OF THE ART

The present invention relates to a blood pressure measuring apparatus for automatically measuring a blood pressure of a living subject based on a variation of a pulse-synchronous signal, such as a Korotkoff sound or a pulse wave, produced while a pressing pressure of a cuff applied to a portion of the living subject is slowly changed.

BACKGROUND OF THE INVENTION

In a conventional blood pressure measuring apparatus, a blood pressure value may be incorrectly determined based on a pulse-synchronous signal inaccurately detected due to noise resulting from, e.g., a body movement, or the like. To avoid such incorrect blood pressure measurement, it is needed to provide the blood pressure measuring apparatus with a high-performance filter circuit or a signal processing device for removing noise from the signal. Otherwise, when it is judged that a blood pressure value obtained in a blood pressure measurement is abnormal, as compared with the previously measured blood pressure values, the blood pressure measuring apparatus needs to go to the initial step of another blood pressure measurement.

Since the above mentioned high-performance filter circuit or signal processing device has a high technique and a complicate construction, the blood pressure measuring apparatus including it has the disadvantage of being complicate and expensive. Additionally, when, after an incorrect blood pressure measurement, another blood pressure measurement is carried out, a patient suffers from discomfort because the pressing pressure of a cuff is applied to the patient again.

The present invention has been developed in the above background. It is an object of the invention to provide a blood pressure measuring apparatus with a simple construction and a low price, which can minimize the discomfort of a patient even when an incorrect blood pressure value is measured due to noise or the like.

DISCLOSURE OF THE INVENTION

The above object may be achieved according to a first invention which provides a blood pressure measuring apparatus for automatically measuring a blood pressure of a living subject based on a variation of a pulse-synchronous signal produced from an artery of the living subject while a pressing pressure of a cuff applied to a portion of the living subject is slowly changed by a cuff-pressure regulating means, the blood pressure measuring apparatus being characterized by comprising: (a) first blood pressure determining means for determining a first blood pressure value of the subject based on a variation of the pulse-synchronous signal produced while the pressure of the cuff is slowly increased; (b) second blood pressure determining means for determining a second blood pressure value of the subject based on a variation of the pulse-synchronous signal produced while the pressure of the cuff is slowly decreased; and (c) blood-pressure-abnormality judging means for judging whether the first blood pressure value determined by the first blood pressure determining means is abnormal, the blood-pressure-abnormality judging means commanding the cuff-pressure regulating means to quickly decrease the pressure of the cuff, when the first blood pressure value is not abnormal, the blood-pressure-abnormality judging means commanding the cuff-pressure regulating means to slowly decrease the pressure of the cuff increased for the blood pressure determination of the first blood pressure determining means, for the blood pressure determination of the second blood pressure determining means, when the first blood pressure value is abnormal.

In the above mentioned blood pressure measuring apparatus, when it is judged by the blood-pressure-abnormality judging means that the first blood pressure value determined by the first blood pressure determining means while the pressure of the cuff is slowly increased is abnormal, the pressure of the cuff is slowly decreased for the blood pressure determination of the second blood pressure determining means. According to the first invention, even when the first blood pressure value determined by the first blood pressure determining means is abnormal due to noise generated during the slow increasing of the pressure of the cuff, the present blood pressure measuring apparatus can end the blood pressure measurement earlier than the conventional blood pressure measuring apparatus which needs to go the initial step of another blood pressure measurement, by the time necessary for decreasing and re-increasing the pressure of the cuff, thereby reducing the discomfort of the patient. Further, since the blood pressure measuring apparatus measures the second blood pressure value relatively speedily, it does not need a device for removing noise from the signal.

Preferably, in the present blood pressure measuring apparatus, each of the first and second blood pressure determining means may execute a blood pressure determining algorithm each time a cuff pulse wave produced in the cuff is obtained while the pressure of the cuff is slowly changed.

Further, in the present blood pressure measuring apparatus, each of the first and second blood pressure determining means may execute a blood pressure determining algorithm when a plurality of cuff pulse waves produced in the cuff are obtained while the pressure of the cuff is slowly changed.

Moreover, the present apparatus may further comprise a blood pressure value indication controlling means which controls a display device to indicate the second blood pressure value determined by the second blood pressure determining means when the second blood pressure value is not abnormal, and which controls the display device to indicate that the first and second blood pressure values are abnormal, when the second blood pressure value is abnormal.

The above object may be achieved according to a second invention which provides a blood pressure measuring apparatus for automatically measuring a blood pressure of a living subject based on a variation of a pulse-synchronous signal produced from an artery of the living subject while a pressing pressure of a cuff applied to a portion of the living subject is slowly changed by a cuff-pressure regulating means, the blood pressure measuring apparatus being characterized by comprising: (a) first blood pressure determining means for determining a first blood pressure value of the subject based on a variation of the pulse-synchronous signal produced while the pressure of the cuff is slowly increased; (b) second blood pressure determining means for determining a second blood pressure value of the subject based on a variation of the pulse-synchronous signal produced while the pressure of the cuff is slowly decreased; and (c) signal-abnormality judging means for judging whether the variation of the pulse-synchronous signal obtained during the slow increasing of the pressure of the cuff is abnormal, the signal-abnormality judging means commanding the cuff-pressure regulating means to quickly decrease the pressure of the cuff, when the variation of the pulse-synchronous signal is not abnormal, the signal-abnormality judging means commanding the cuff-pressure regulating means to slowly decrease the pressure of the cuff increased for the blood pressure determination of the first blood pressure determining means, for the blood pressure determination of the second blood pressure determining means, when the variation of the pulse-synchronous signal is abnormal.

In the above-mentioned blood pressure measuring apparatus, when it is judged by the signal-abnormality judging means that a variation of the pulse-synchronous signal obtained during the slow increasing of the pressure of the cuff is abnormal, the pressure of the cuff is decreased for the blood pressure determination of the second blood pressure determining means. According to the second invention, even when the variation of the pulse-synchronous signal is abnormal due to noise generated during the slow increasing of the pressure of the cuff, the present blood pressure measuring apparatus can end the blood pressure measurement earlier than the conventional blood pressure measuring apparatus which needs to go the initial step of another blood pressure measurement, by the time necessary for decreasing and re-increasing the pressure of the cuff, thereby reducing the discomfort of the patient. Further, since the present blood pressure measuring apparatus measures the second blood pressure value relatively speedily, it does not need a device for removing noise from the signal.

Preferably, the present apparatus may further comprise blood-pressure-abnormality judging means for judging whether the first blood pressure value determined by the first blood pressure determining means is abnormal, the blood-pressure-abnormality judging means commanding the cuff-pressure regulating means to quickly decrease the pressure of the cuff, when the first blood pressure value is not abnormal, the blood-pressure-abnormality judging means commanding the cuff-pressure regulating means to slowly decrease the pressure of the cuff increased for the blood pressure determination of the first blood pressure determining means, for the blood pressure determination of the second blood pressure determining means, when the first blood pressure value is abnormal.

Preferably, in the present apparatus, each of the first and second blood pressure determining means may execute a blood pressure determining algorithm each time a cuff pulse wave produced in the cuff is obtained while the pressure of the cuff is slowly changed.

Preferably, in the present apparatus, each of the first and second blood pressure determining means may execute a blood pressure determining algorithm when a plurality of cuff pulse waves produced in the cuff are obtained while the pressure of the cuff is slowly changed.

Further, the present apparatus may further comprise a blood pressure value indication controlling means which controls a display device to indicate the second blood pressure value determined by the second blood pressure determining means when the second blood pressure value is not abnormal, and which controls the display device to indicate that the first and second blood pressure values are abnormal, when the second blood pressure value is abnormal.

THE BEST MODE FOR CARRYING OUT THE INVENTION

Figure 1:
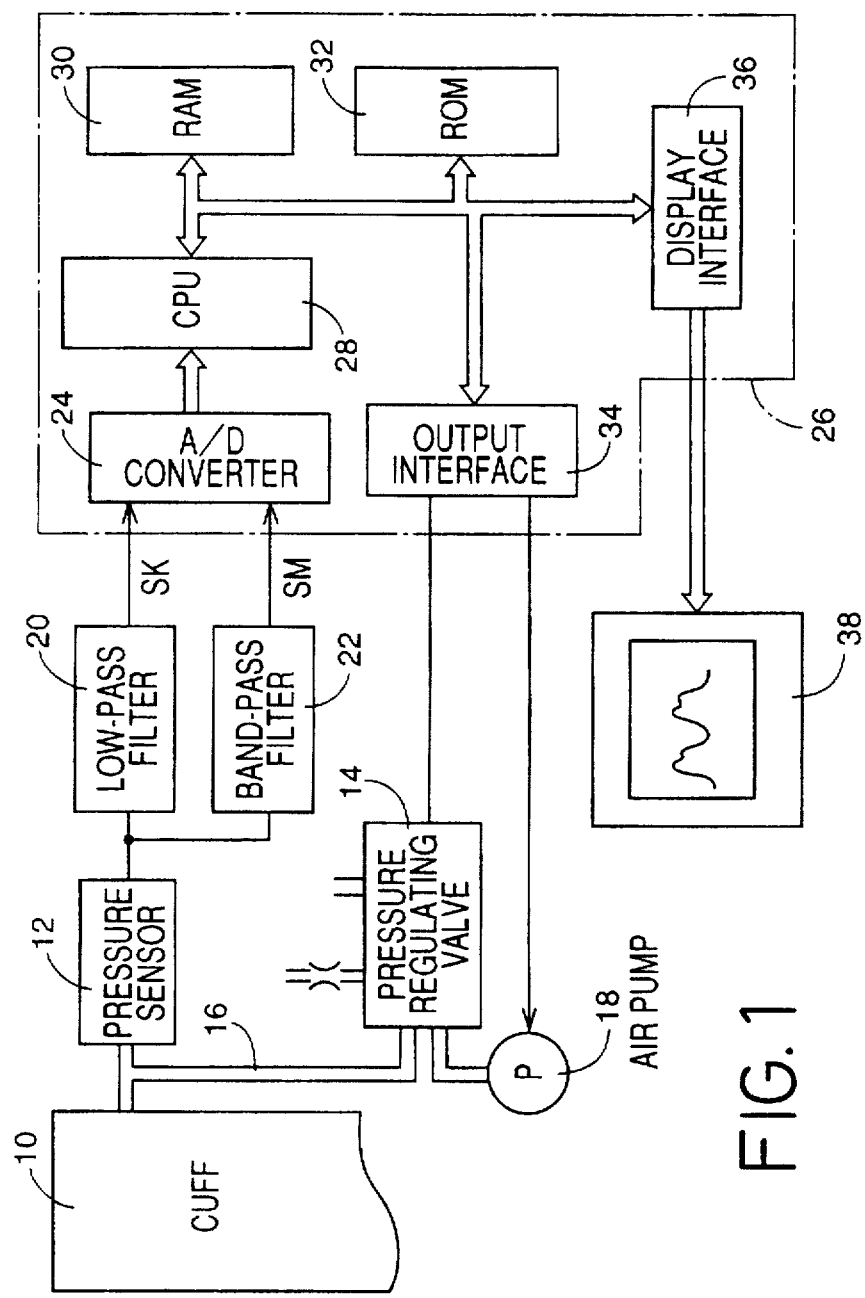
FIG. 1 is a diagrammatic view for illustrating the construction of a blood pressure measuring apparatus embodying the present invention.

There will be described in detail an oscillometric-type automatic blood pressure measuring apparatus as an embodiment of the present invention, referring to the drawings.

In FIG. 1, the blood pressure measuring apparatus includes a belt-like cuff 10 which is adapted to be wound for pressing an upper arm of a living subject and which is provided by a bag formed of an elastic sheet such as rubber or vinyl, and additionally includes a pressure sensor 12 and a pressure regulating valve 14 each of which is connected to the cuff 10 via a piping 16.

The pressure sensor 12 includes a semiconductor pressure sensing element, for example. The pressure sensor 12 detects a pressure in the cuff 10, and supplies a pressure signal SP representative of the detected pressure to each of a low-pass filter 20 and a band-pass filter 22. The low-pass filter 20 extracts, from the pressure signal SP, a static pressure component contained in the signal SP, i.e., cuff pressure signal SK representative of a cuff pressure $P_c$. The cuff pressure signal SK is transmitted to an A/D converter 24. On the other hand, the band-pass filter 22 extracts, from the pressure signal SP, a cuff pulse wave component having predetermined frequences, such as 0.3 to 30 Hz, i.e., cuff pulse wave signal SM representative of a cuff pulse wave. The cuff pulse wave signal SM is transmitted to the A/D converter 24. The cuff pulse wave is an oscillatory pressure wave which is produced in the cuff 10 wound around the upper arm of the subject because of a pulsation of an artery of the arm in synchronism with the heartbeat of the subject. The A/D converter 24 includes a multiplexer which receives, by time sharing, each of the two input signals, and concurrently converts the two signals into corresponding digital signals, respectively.

The control device 26 is provided by a so-called microcomputer including a CPU 28, a ROM 30, a RAM 32, an output interface 34, and a display interface 36. The CPU 28 processes input signals according to control programs pre-stored in the ROM 32 by utilizing a temporary-storage function of the RAM 30. The CPU 28 of the control device 26 supplies drive signals to an air pump 18 and the pressure regulating valve 14 through the output interface 34, and to a display device 38 through the display interface 38. The display device 38 includes an image display panel for displaying numerical values and/or waveforms on a number of light-emitting elements and a printer for printing the numerical values and/or the waveforms on a sheet of paper with an ink.

Figure 2:
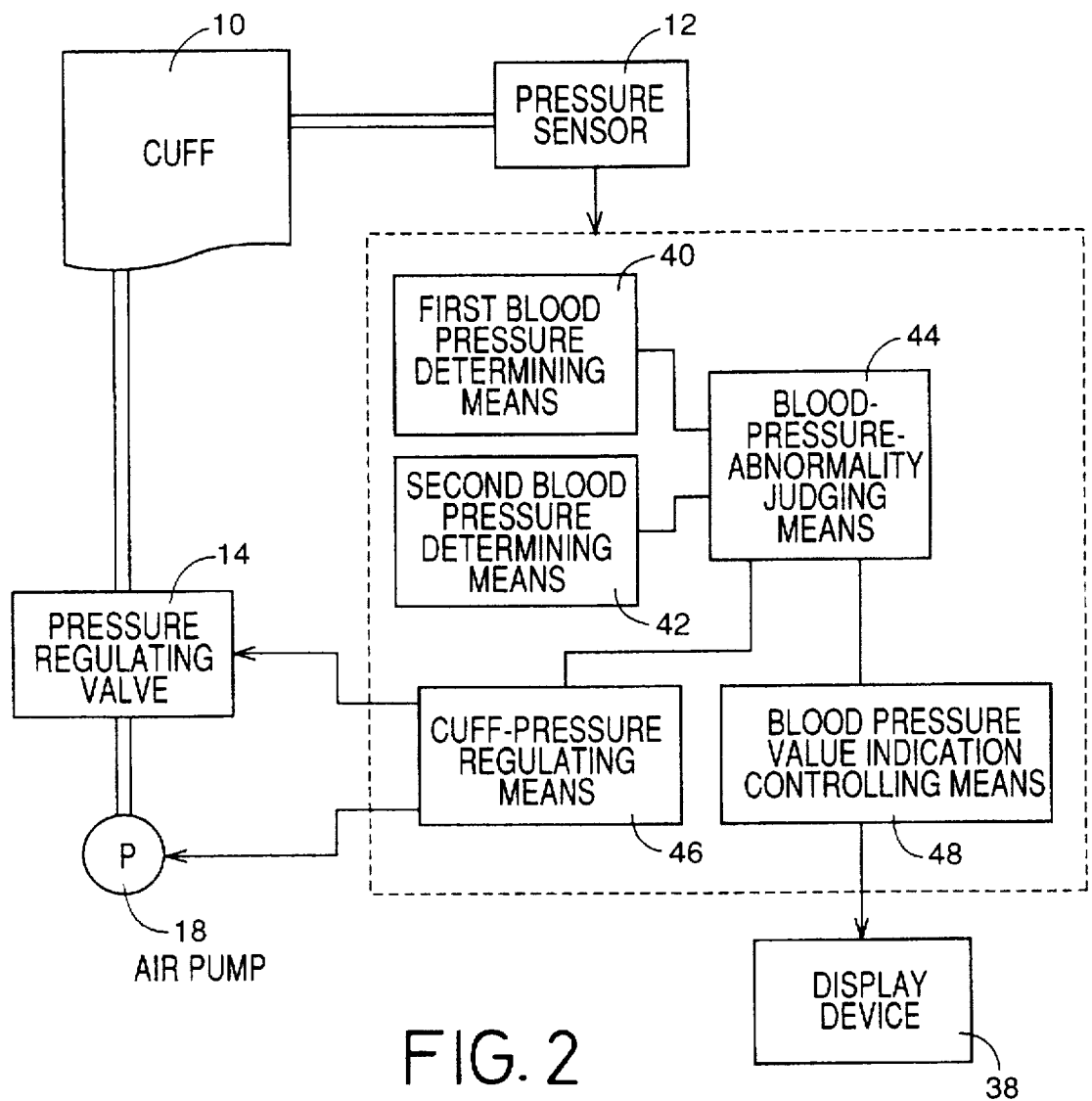
FIG. 2 is a block diagram for explaining various functions of a control device 26 of the apparatus of FIG. 1.

FIG. 2 is a block diagram for explaining various functions of the control device. 26. In the figure, the pressure sensor 12 detects a cuff pulse wave produced, in synchronism with the heartbeat of the subject, in the cuff 10 wound on a portion of the subject while a pressure of the cuff 10 is changed. A cuff-pressure regulating means 46 commands the pressure regulating valve 14 and the air pump 18 to change the cuff pressure. A first blood pressure determining means 40 determines one or more first blood pressure values, such as systolic or maximum,and diastolic or minimum blood pressure values, based on the variation of respective amplitudes of the cuff pulse waves produced while the pressure of the cuff 10 is slowly increased by the cuff pressure regulating means 46., according to a so-called oscillometric method. A second blood pressure determining means 42 determines one or more second blood pressure values, such as systolic and diastolic blood pressure values, based on the variation of respective amplitudes of the cuff pulse waves produced while the pressure of the cuff 10 is slowly decreased by the cuff pressure regulating means 46, according to the oscillometric method. A blood-pressure-abnormality judging means 44 judges whether the first blood pressure values determined by the first blood pressure determining means are abnormal. When the first blood pressure values are abnormal, the second blood pressure determining means 42 determines second blood pressure values. A blood pressure value indication controlling means 48 controls the display device 38 to indicate the first or second blood pressure value determined by the first or second blood pressure determining means 40, 42 when the first or second blood pressure values are not abnormal, and to indicate that the second blood pressure values are abnormal, when the second blood pressure values are abnormal.

Figure 3:
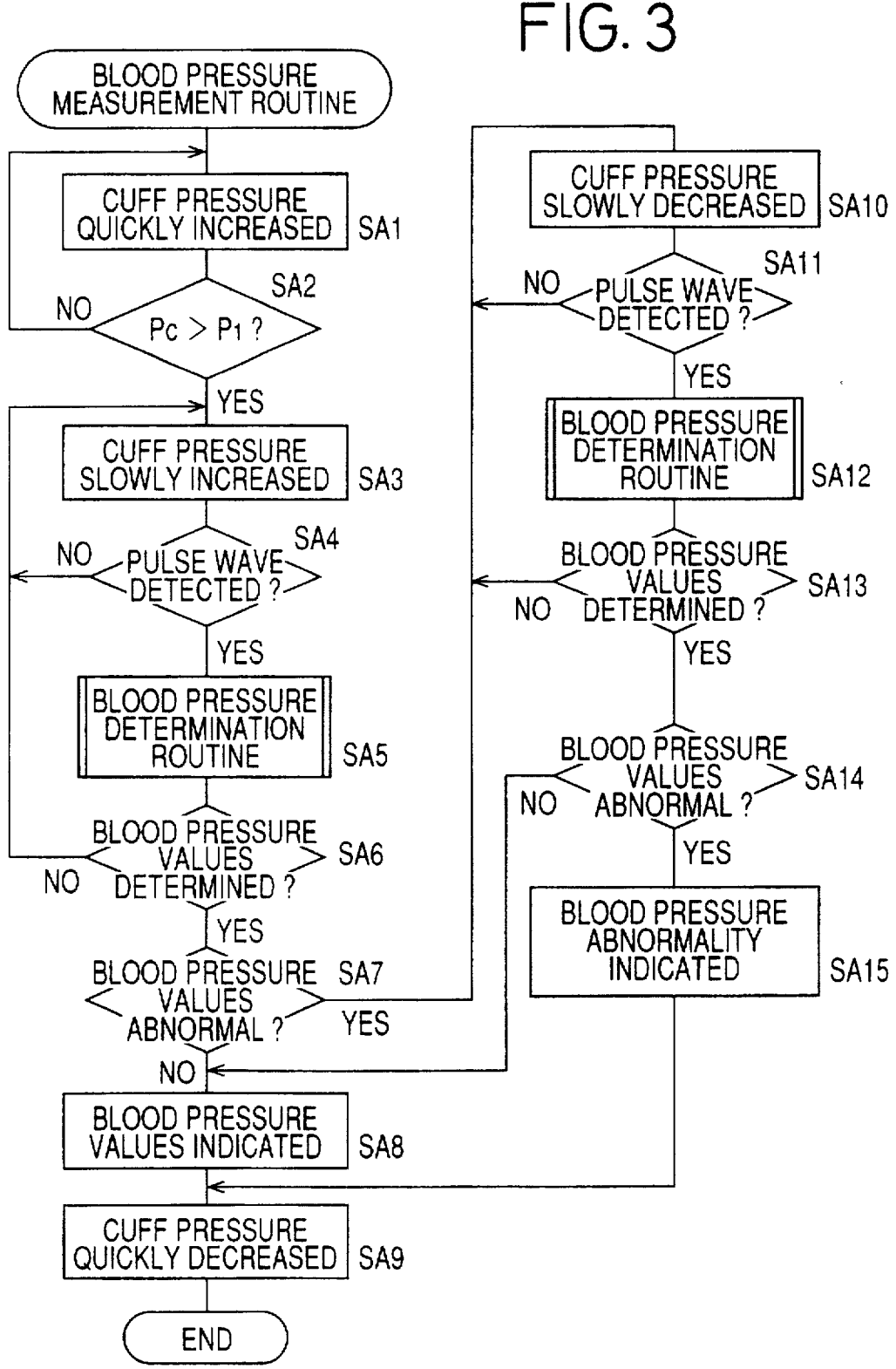
FIG. 3 is a flow chart representing the operation of the control device 26 of the apparatus of FIG. 1.

FIG. 3 is a flow chart representing the operation of the control device 26. When a start switch (not shown) is pushed ON for a blood pressure measurement, Step SA1 is carried out. At Step SA1, the pressure regulating valve 14 is placed in a quick-inflation position in which the pressure regulating valve 14 permits a pressurized air to be quickly supplied to the cuff 10 by the air pump 18, as shown at point $t_1$ in FIG. 4. Step SA1 is followed by Step SA2 to judge whether or not the pressure in the cuff, i.e., cuff pressure $P_c$ is higher than a predetermined value $P_1$, for example, 50 mmHg, which is lower than the diastolic blood pressure value of the subject. If a negative judgment is made at Step SA2, the control of CPU 28 repeats Step SA1. If a positive judgment is made at Step SA2, the control of CPU 28 goes to Step SA3. At Step SA3, the pressure regulating valve 14 is switched to a slow-inflation position in which the pressure regulating valve 14 permits the pressurized air to be supplied to the cuff 10 at a rate suitable for blood pressure measurements, for example, 2 to 3 mmHg/sec, as shown at point $t_2$ in FIG. 4.

Step SA3 is followed by Step SA4 to judge whether or not a cuff pulse wave has been detected, based on the pulse wave signal SM. If a negative judgment is made at Step SA4, the control of CPU 28 goes back to Step SA3. If a positive judgment is made at Step SA4, the control of CPU 28 goes to Step SA5, corresponding to the first blood pressure determining means 40, to carry out a blood pressure determination routine. In this routine, one or more first blood pressure values, such as systolic, mean and diastolic blood pressure values $P_{max}$, $P_{mean}$, $P_{min}$, are determined, based on a difference between respective amplitudes of each pair of successive cuff pulse waves detected by the band-pass filter 22 while the cuff pressure $P_c$ is slowly increased, according to a well-known oscillometric-type blood pressure determining algorithm. Step SA5 is followed by Step SA6 to judge whether or not the first blood pressure values have been determined. If a negative judgment is made at Step SA6, Steps SA3 to SA6 are repeated and the slow increasing of the cuff pressure $P_c$ is continued.

If a positive judgment is made at Step SA6, the control of the CPU 28 goes to Step SA7, corresponding to the blood-pressure-abnormality judging means 44, to judge whether or not the first blood pressure values determined at Step SA5 are abnormal. To judge whether or not the first blood pressure values are abnormal, the following expression (1) which has been found by experience is used, for example.

$$P_{mean} = P_{min} + \frac{P_{max} - P_{min}}{3} \quad (1)$$

Figure 4:
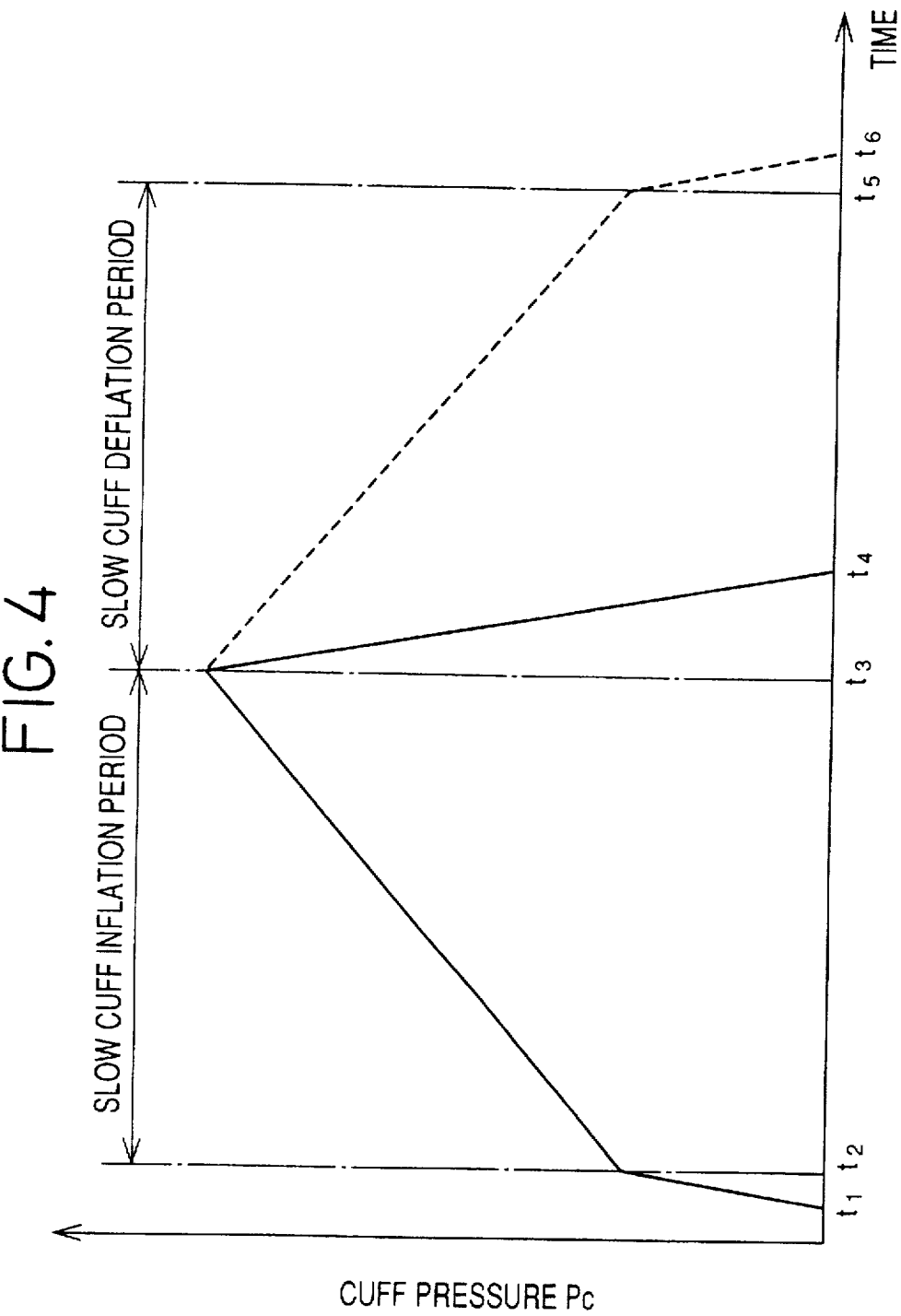
FIG. 4 is a time chart showing the operation of the control device 26 of the apparatus of FIG. 1.

At Step SA7, the CPU judges whether or not the above expression (1) holds for the first blood pressure values determined at Step SA5. If a negative judgment is made at Step SA7, the control of the CPU 28 goes to Step SA8 to indicate the first blood pressure values on the display device 38. Step SA8 is followed by Step SA9 to stop the air pump 18 and switch the pressure regulating valve 14 to a quick-deflation position in which the pressurized air is quickly deflated from the cuff 10. Thus, the present routine is terminated. Point $t_3$ in FIG. 4 shows the time when the routine has thus been ended and point $t_4$ shows the time when the deflation of the cuff 10 has been completed.

Meanwhile, if a positive judgment is made at Step SA7, the control of the CPU 28 goes to Step SA10. At Step SA10, the pressure regulating valve 14 is switched to a slow-deflation position in which the cuff pressure $P_c$ is slowly decreased at a rate suitable for blood pressure measurements, for example, 2 to 3 mmHg/sec, as indicated at broken line in FIG. 4. Step SA10 is followed by Step SA11 to judge whether or not a cuff pulse wave has been detected, similarly to Step SA4. If a negative judgment is made at Step SA 11, Steps SA10 and SA11 are repeated. If a positive judgment is made at Step SA11, the control of the CPU 28 goes to Step SA12 corresponding to the second blood pressure determining means 42. At Step SA12, a similar blood pressure determination routine is carried out to determine one or more second blood pressure values.

Step SA12 is followed by Step SA13, similar to Step SA6, to judge whether or not the determination of the second blood pressure values has been completed. If a negative judgment is made at Step SA13, Steps SA10 to SA13 are repeated. If a positive judgment is made at Step SA13, the control of the CPU goes to Step SA14 to judge whether or not the second blood pressure values are abnormal. If a negative judgment is made at Step SA14, the control of the CPU 28 goes back to Steps SA8 and SA9. At Step SA8, the second blood pressure values are indicated on the display device 38. At Step SA9, the air pump 18 is stopped and the pressure in the cuff 10 is quickly decreased. Thus, the present routine is terminated. However, if a positive judgment is made at Step SA14, the control of the CPU 28 goes to Step SA15 to indicate, on the display device 38, that the blood pressure values are abnormal. Step SA15 is followed by Step SA9 to stop the air pump 18 and quickly decrease the pressure in the cuff 10. Thus, the present routine is terminated. Point $t_5$ in FIG. 4 shows the time when the present routine has thus been ended and point $t_6$ shows the time when the deflation of the cuff 10 has been completed. In this embodiment, Steps SA1, SA3, SA9 and SA10 correspond to the cuff-pressure regulating means 46, and Steps SA8, SA14 and SA15 correspond to the blood pressure indication controlling means 48.

In the above described oscillometric-type automatic blood pressure measuring apparatus, when, at Step SA7 corresponding to the blood-pressure-abnormality judging means 44, the CPU 28 judges that the first blood pressure values are abnormal due to noise resulting from a body movement, or the like, while the cuff pressure $P_c$ is slowly increased, at Step SA12 corresponding to the second blood pressure determining means 42, second blood pressure values are determined while the cuff pressure $P_c$ is slowly decreased. Thus, it is not needed to decrease and re-increase the pressure of the cuff 10 for another blood pressure measurement, thereby reducing the blood pressure measurement time. The reduction of the blood pressure measurement time leads to the reduction of the discomfort of a patient.

Further, since the present oscillometric blood pressure measuring apparatus can measure second blood pressure values relatively speedily, it does not need a complicate and expensive device for removing noise. Thus, the present invention provides a simpler and cheaper oscillometric-type automatic blood pressure measuring apparatus.

In the above described embodiment, the amount of increasing of the cuff pressure during the initial quick inflation is relatively small and the amount of decreasing of the cuff pressure during the final quick deflation is relatively small, in comparison with a blood pressure measuring apparatus which determines a blood pressure value while the pressure of a cuff 10 is slowly decreased and, when the determined blood pressure value is judged abnormal, determines a blood pressure value while the cuff pressure is slowly increased. Therefore, the time necessary for the quick inflation and quick deflation of the cuff 10 is reduced, so that it is possible to shorten the blood pressure measurement time. Further, since, in the present apparatus, it is not required to increase the pressure of the cuff 10 to a value higher than the systolic blood pressure value of the patient, the discomfort of a patient is minimized.

Next, there will be described another embodiment according to the present invention. Hereinafter, the same parts as those of the prior embodiment will be denoted by the same reference numerals and the description thereof is omitted.

Figure 5:
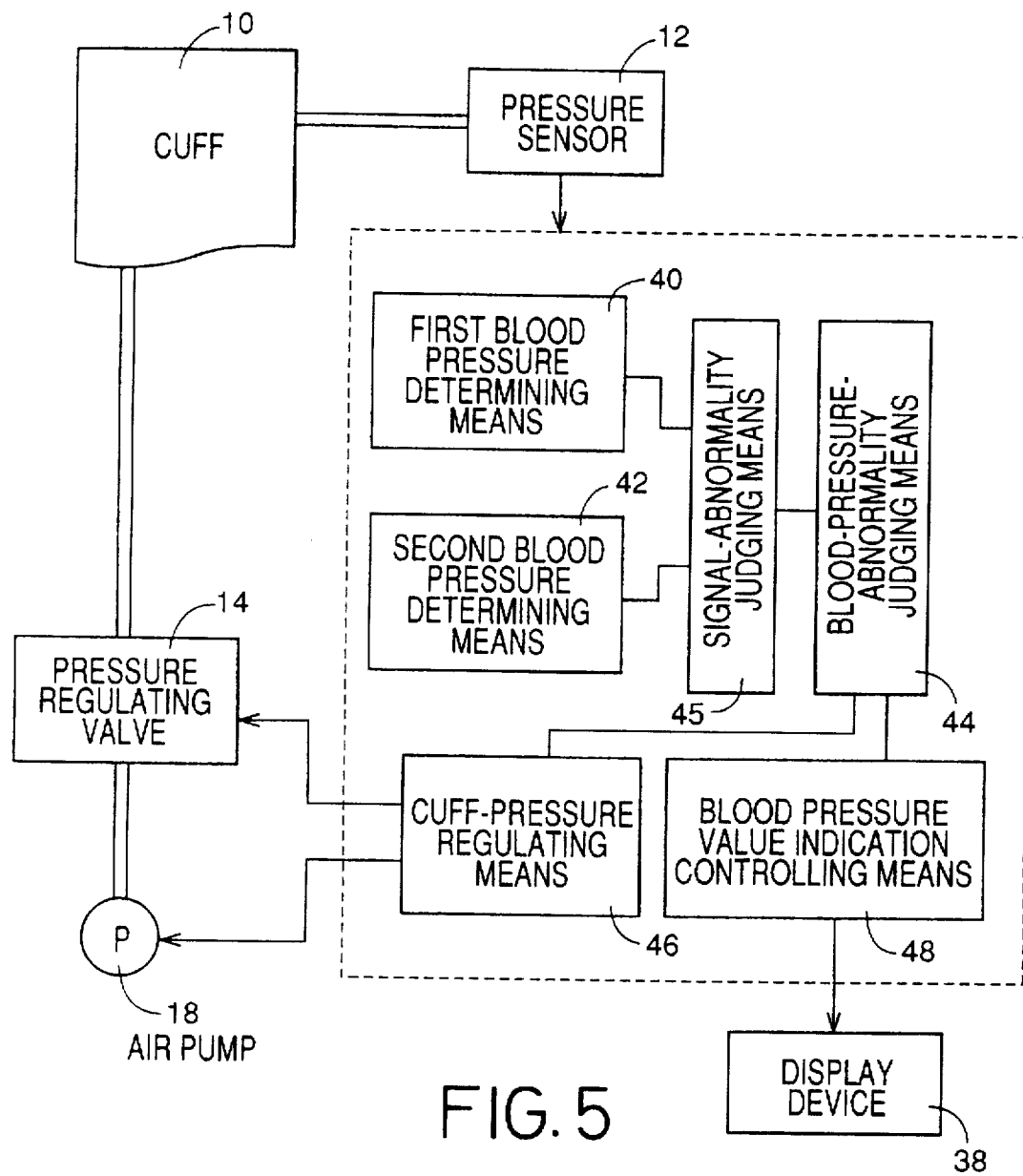
FIG. 5 is a block diagram for explaining various functions of a blood pressure measuring apparatus as another embodiment according to the present invention.

FIG. 5 is a block diagram for explaining various functions of a blood pressure measuring apparatus as another embodiment according to the present invention. In the figure, a signal-abnormality judging means 45 judges whether or not the variation of the pulse wave signal SM obtained during the slow increasing of the pressure of the cuff 10 is abnormal to an extent inappropriate for a blood pressure measurement. If a negative judgment is made, the signal-abnormality judging means 45 commands the cuff-pressure regulating means 46 to quickly decrease the pressure of the cuff 10. If a positive judgment is made, the second blood pressure determining means 42 determines second blood pressure vales.

Figure 6:
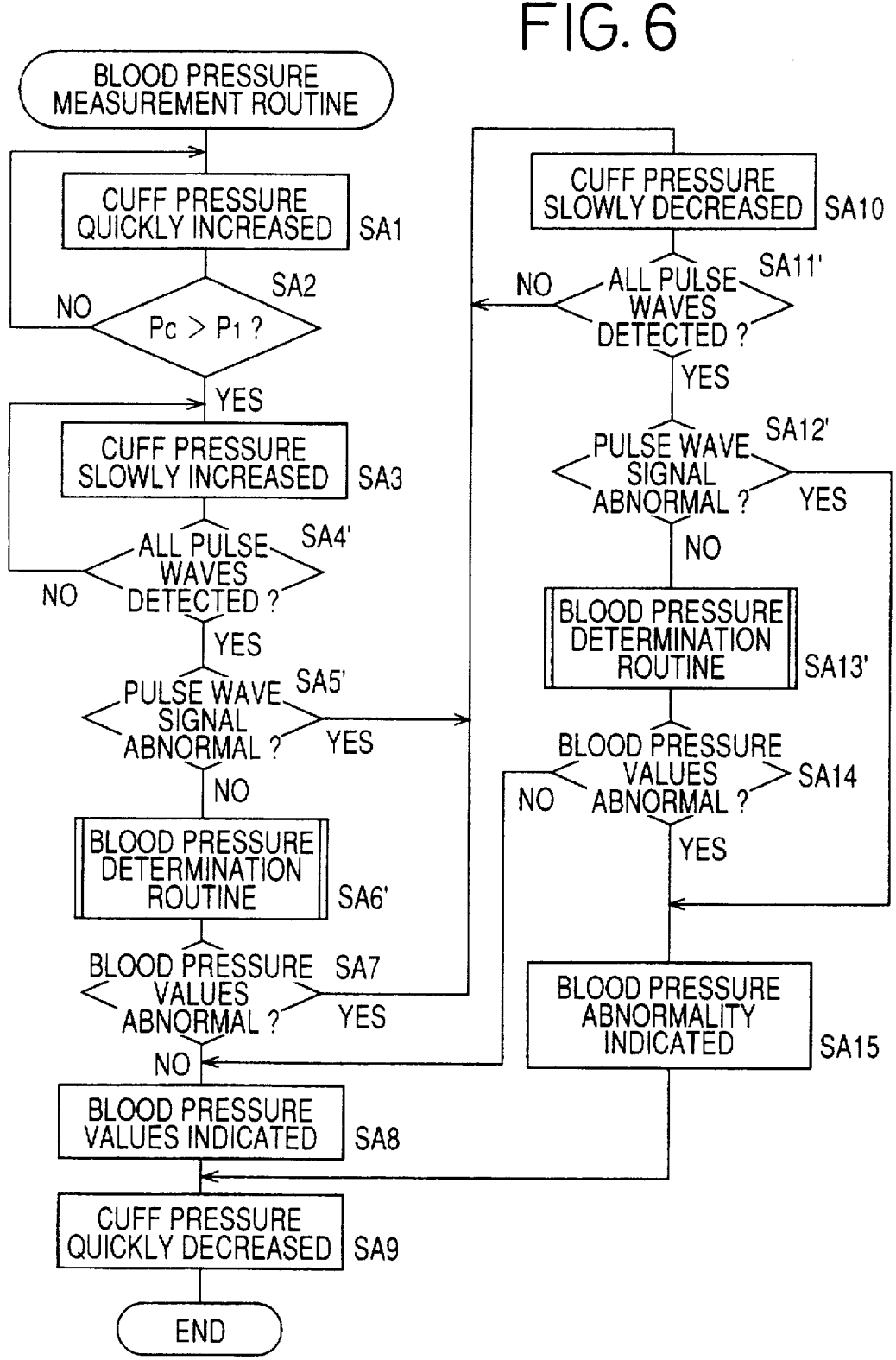
FIG. 6 is a flow chart representing the operation of a control device 26 of the apparatus of FIG. 5.

FIG. 6 is a flow chart representing the operation of a control device 26 in the present embodiment. In the figure, Steps SA1 to SA3 are carried out similarly to Steps SA1 to SA3 of the prior embodiment. Step SA3 is followed by Step SA4' to temporarily store all the pulse wave signal SM produced while the pressure of the cuff 10 is increased, and to judge that all the pulse waves have been detected when a point of inflection (i.e., a maximum of the differences between the respective amplitudes of each pair of successive pulse waves) is detected, during the decreasing of respective amplitudes of the pulse waves. Concurrently, at Step SA4', the CPU 28 judges that all the pulse waves have been detected when a predetermined time period long enough to detect the pulse wave signal has been measured by a guard timer.

Step SA4' is followed by Step SA5', corresponding to the signal-abnormality judging means 45, to judge whether or not the series of pulse waves represented by the pulse wave signal SM obtained during the slow increasing of the pressure of the cuff 10 are abnormal to such an extent that the current blood pressure measurement is unsuccessful. For example, it is judged that the pulse wave signal is not abnormal when the number of the pulse waves obtained during the increasing of respective amplitudes of the pulse waves and the number of the pulse waves obtained during the subsequent decreasing of respective amplitudes of the pulse waves is equal to or larger than five or six.

If a negative judgment is made at Step SA5', the control of the CPU 28 goes to Step SA6' corresponding to the first blood pressure determining means 40. At Step SA6', a blood pressure determination routine is carried out. In the routine, one or more first blood pressure values, such as systolic, mean and diastolic blood pressure values $P_{max}$, $P_{mean}$ and $P_{min}$, are determined based on the respective amplitudes of all the pulse waves which are detected during the slow increasing of the cuff pressure $P_c$ and temporarily stored, according to a well-known oscillometric-type blood pressure measuring algorithm for determining one or more blood pressure values, such as systolic, mean and diastolic blood pressure values, based on the difference between respective amplitudes of each pair of successive pulse waves.

Subsequently, Step SA6' is followed by Step SA7. Like the prior embodiment, at Step SA7, the CPU 28 judges whether or not the measured first blood pressure values are abnormal. If a negative judgment is made at Step SA7, the control of the CPU 28 goes to Steps SA8 and SA9. At Step SA8, the first blood pressure values are displayed. At Step SA9, the pressure of the cuff 10 is quickly decreased.

If a positive judgment is made at one of Steps SA5' and SA7, the control of the CPU 28 goes to Step SA10 to slowly decrease the pressure of the cuff 10 similarly to Step SA10 of the prior embodiment. Step SA10 is followed by Steps SA11' to SA13' to determine one or more second blood pressure values during the decreasing of the pressure of the cuff 10 similarly to the first blood pressure values. Thus, in the present embodiment, it is possible to obtain the same advantages as those of the prior embodiment.

The blood pressure measuring apparatus according to the above mentioned second embodiment includes the blood-pressure-abnormality judging means 44 for commanding the second blood pressure determining means 42 to determine second blood pressure values when the first blood pressure values determined by the first blood pressure determining means 40 are abnormal, besides the signal-abnormality judging means 45 for commanding the second blood pressure determining means 42 to determine second blood pressure values when the signal obtained for the blood pressure determination of the first blood pressure determining means 40 is abnormal. Thus, the present apparatus has the advantage of obtaining a more reliable blood pressure value.

While the present invention has been described in its preferred embodiments by reference to the drawings, it is to be understood that the invention may otherwise be embodied.

For example, in the illustrated embodiments, the pulse waves used for determining blood pressure values are detected while the cuff pressure is slowly changed at a predetermined rate, that is, linearly. However, the pulse waves for determining the blood pressure values may be detected while the cuff pressure $P_c$ is substantially slowly changed by alternately repeating a first operation in which the cuff pressure is increased by a predetermined amount and a second operation in which the increased cuff pressure is held for a predetermined time, that is, by changing the cuff pressure $P_c$ stepwise.

In the blood pressure determination routine carried out at Step SA5 or SA12, systolic and diastolic blood pressure values may be determined based on the occurrence and disappearance of blood-flow sounds which are detected by a microphone from a brachial artery of the subject while the cuff pressure $P_c$ is slowly changed, according to a well-known Korotkoff-sound type blood pressure determining algorithm for determining systolic and diastolic blood pressure values. Further, the blood pressure determination routine may be carried out by utilizing a pulse wave produced by the pulsation from the wall of an artery downstream of the body portion pressed by the cuff 10, based on the reflection of an ultrasonic wave from the arterial wall, according to an oscillometric method. At any rate, a blood pressure value may be determined based on a pulse-synchronous wave signal produced while the cuff pressure $P_c$ is substantially slowly changed.

When, at Step SA14, it is judged that the second blood pressure values are abnormal, the control of the CPU 28 may automatically return to Step SA1 for carrying out another blood pressure measurement, without indicating that the second blood pressure values are abnormal.

While, in the embodiment shown in FIGS. 5 and 6, the blood-pressure-abnormality judging means 44 and Step SA7 corresponding thereto may be omitted.

It is to be understood that the present invention may be embodied with other modifications or improvements which may occur to those skilled in the art without departing from the scope of the invention.

INDUSTRIAL UTILITY

It will be understood from the above description that since the blood pressure measuring apparatus according to the present invention is able to minimize the discomfort of a patient, it is suitable for use at a clinic for outpatients, a public health center, or the like, where a blood pressure measurement is carried out.

We claim:

1. A blood pressure measuring apparatus for automatically measuring a blood pressure of a living subject based on a variation of a pulse-synchronous signal produced from an artery of the living subject while a pressing pressure of a cuff applied to a portion of the living subject is slowly changed, the blood pressure measuring apparatus comprising:

cuff-pressure regulating means for changing the pressing pressure of the cuff applied to the portion of the living subject;

first blood pressure measuring determining means for determining a first blood pressure value of the subject based on a variation of the pulse synchronous signal produced while the pressure of said cuff is slowly increased;

second blood pressure determining means for determining a second blood pressure value of the subject based on a variation of the pulse-synchronous signal produced while the pressure of said cuff is slowly decreased;

blood-pressure-abnormality judging means for judging whether the first blood pressure value determined by said first blood pressure determining means is abnormal, said blood pressure-abnormality judging means commanding said cuff-pressure regulating means to quickly decrease the pressure of said cuff, when said first blood pressure value is not abnormal, said blood-pressure-abnormality judging means commanding said cuff-pressure regulating means to slowly decrease the pressure of said cuff increased for the first blood pressure determination of said first blood pressure determining means, for the blood pressure determination of said second blood pressure determining means, when said first blood pressure is abnormal.

2. A blood pressure measuring apparatus according to claim 1, wherein each of said first and second blood pressure determining means executes a blood pressure determining algorithm each time a cuff pulse wave produced in said cuff is obtained while the pressure of said cuff is slowly changed.

3. A blood pressure measuring apparatus according to claim 1, wherein each of said first and second blood pressure determining means executes a blood pressure determining algorithm when a plurality of cuff pulse waves produced in said cuff are obtained while the pressure of said cuff is slowly changed.

4. A blood pressure measuring apparatus according to claim 1, further comprising a blood pressure value indication controlling means which controls a display device to indicate the second blood pressure value determined by said second blood pressure determining means when the second blood pressure value is not abnormal, and which controls the display device to indicate that the first and second blood pressure values are abnormal, when the second blood pressure value is abnormal.

5. A blood pressure measuring apparatus for automatically measuring a blood pressure of a living subject based on a variation of a pulse-synchronous signal produced from an artery of the living subject while a pressing pressure of a cuff applied to a portion of the living subject is slowly changed, the blood pressure measuring apparatus comprising:

cuff-pressure regulating means for changing the pressing pressure of the cuff applied to the portion of the living subject;

first blood pressure measuring determining means for determining a first blood pressure value of the subject based on a variation of the pulse synchronous signal produced while the pressure of said cuff is slowly increased;

second blood pressure determining means for determining a second blood pressure value of the subject based on a variation of the pulse-synchronous signal produced while the pressure of said cuff is slowly decreased;

signal-abnormality judging means for judging whether the variation of the pulse synchronous signal obtained during the slow increasing of the pressure of said cuff is abnormal, said signal-abnormality judging means commanding said first blood pressure determining means to determine said first blood pressure value when the variation of the pulse-synchronous signal is not abnormal, said signal-abnormality judging means commanding said cuff-pressure regulating means to slowly decrease the pressure of said cuff increased for the first blood pressure determination of said first blood pressure determining means, for the blood pressure determination of said second blood pressure determining means, when the variation of said pulse synchronous signal is abnormal.

6. A blood pressure measuring apparatus according to claim 5, further comprising blood-pressure-abnormality judging means for judging whether the first blood pressure value determined by said first blood pressure determining means is abnormal, said blood-pressure-abnormality judging means commanding said cuff-pressure regulating means to quickly decrease the pressure of said cuff, when said first blood pressure value is not abnormal, said blood-pressure-abnormality judging means commanding said cuff-pressure regulating means to slowly decrease the pressure of said cuff increased for the blood pressure determination of said first blood pressure determining means, for the blood pressure determination of said second blood pressure determining means, when said first blood pressure value is abnormal.

7. A blood pressure measuring apparatus according to claim 5, wherein each of said first and second blood pressure determining means executes a blood pressure determining algorithm each time a cuff pulse wave produced in said cuff is obtained while the pressure of said cuff is slowly changed.

8. A blood pressure measuring apparatus according to claim 5, wherein each of said first and second blood pressure determining means executes a blood pressure determining algorithm when a plurality of cuff pulse waves produced in said cuff are obtained while the pressure of said cuff is slowly changed.

9. A blood pressure measuring apparatus according to claim 5, further comprising a blood pressure value indication controlling means which controls a display device to indicate the second blood pressure value determined by said second blood pressure determining means when the second blood pressure value is not abnormal, and which controls the display device to indicate that the first and second blood pressure values are abnormal, when the second blood pressure value is abnormal.

* * * * *

UNITED STATES PATENT AND TRADEMARK OFFICE
CERTIFICATE OF CORRECTION

PATENT NO. : 5,759,157
DATED : June 2, 1998
INVENTOR(S) : Harada, et al.

It is certified that error appears in the above-identified patent and that said Letters Patent is hereby corrected as shown below:

Column 10, line 34, delete "measuring"

Signed and Sealed this

Sixteenth Day of February, 1999

Attest:

Attesting Officer

Acting Commissioner of Patents and Trademarks